(12) United States Patent
Sato et al.

(10) Patent No.: US 6,821,229 B2
(45) Date of Patent: Nov. 23, 2004

(54) WALKING SUPPORT SYSTEM

(75) Inventors: Tomio Sato, Hiraka-machi (JP); Kenji Nishibayashi, Tokyo-To (JP); Naotaka Kajiya, Kuji (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 10/645,615

(22) Filed: Aug. 22, 2003

(65) Prior Publication Data

US 2004/0043869 A1 Mar. 4, 2004

(30) Foreign Application Priority Data

Aug. 30, 2002 (JP) ........................................ 2002-252526
Aug. 30, 2002 (JP) ........................................ 2002-252527

(51) Int. Cl.[7] .............................................. A63B 21/00
(52) U.S. Cl. .............................. 482/8; 482/9; 482/900; 601/23
(58) Field of Search ........................ 482/1–9, 900–902, 482/51; 601/23

(56) References Cited

U.S. PATENT DOCUMENTS

| | | | |
|---|---|---|---|
| 5,891,042 A | | 4/1999 | Sham et al. |
| 6,135,951 A | * | 10/2000 | Richardson et al. ........ 600/300 |
| 6,571,200 B1 | * | 5/2003 | Mault ......................... 702/182 |
| 6,736,759 B1 | * | 5/2004 | Stubbs et al. ................ 482/8 |

FOREIGN PATENT DOCUMENTS

| | | |
|---|---|---|
| EP | 0 700 661 A2 | 3/1996 |
| EP | 1 127 542 A2 | 8/2001 |
| JP | 5-220120 | 8/1993 |
| JP | 7-313474 | 12/1995 |
| JP | 7-327942 | 12/1995 |
| JP | 7-333367 | 12/1995 |
| JP | 8-24367 | 1/1996 |
| JP | 2000-316833 A | 11/2000 |
| JP | 3247183 | 11/2001 |

* cited by examiner

Primary Examiner—Glenn E. Richman
(74) Attorney, Agent, or Firm—McDermott Will & Emery LLP

(57) ABSTRACT

There is provided a system capable of estimating biological data such as a pulse at the time of walking (exercise) with good reproducibility. Biological data at the time of walking is estimated indirectly by acquiring a relationship between biological data and exercise stress levels in body burden capacity acquiring means 21 prior to walking, acquiring an exercise stress level at the time of walking in means 22 for acquiring an exercise stress level at the time of walking, and relating the exercise stress level at the time of walking to the relationship between biological data and exercise stress levels in means 23 for estimating biological data at the time of walking. Further, a walking amount is also computed by use of the biological data at the time of walking in walking amount computing means 24.

25 Claims, 9 Drawing Sheets

FIG.7

MALES CASE

| EVALUATION / AGE | SIGNIFICANTLY POOR | POOR | NORMAL | SUPERIOR | SIGNIFICANTLY SUPERIOR | CONSIDERABLY SUPERIOR |
|---|---|---|---|---|---|---|
| 19~24 | ~116 | 117~135 | 136~153 | 154~172 | 173~191 | 192~ |
| 25~29 | ~112 | 113~130 | 131~149 | 150~168 | 169~187 | 188~ |
| 30~34 | ~108 | 109~126 | 127~145 | 146~164 | 165~183 | 184~ |
| ⋮ | ⋮ | ⋮ | ⋮ | ⋮ | ⋮ | ⋮ |
| 60~64 | ~83 | 84~102 | 103~121 | 122~139 | 140~158 | 159~ |
| 65~69 | ~79 | 80~98 | 99~117 | 118~135 | 136~154 | 155~ |

PWC75%HRmax

WALKING SUPPORT SYSTEM

BACKGROUND OF THE INVENTION (i) Field of the Invention

The present invention relates to a walking support system which makes supports associated with biological data such as a pulse at the time of walking. More specifically, it relates to a system for estimating biological data at the time of walking which is a type of the foregoing walking support system and estimates biological data at the time of walking. Much more specifically, it relates to a walking pitch generator which is a type of the foregoing walking support system and generates walking pitches to obtain desired biological data such as a pulse rate at the time of walking.

(ii) Description of the Related Art

As one of supports associated with biological data such as a pulse at the time of walking, measurements of biological data such as a pulse which changes by walking (exercise) have heretofore been practiced. In the measurements of the biological data such as a pulse which changes by walking (exercise), a sensor capable of detecting a biological signal which changes by an exercise is attached directly to a living body every time the measurement is made.

Further, as one of supports associated with biological data such as a pulse at the time of walking, a walking pace generator has heretofore been available. This conventional walking pace generator causes a walker to walk in line with a sound or the like generated in synchronization with a preset walking pace.

However, the measurement using the sensor capable of detecting the biological signal which changes by an exercise has a problem that since the sensor receives the signal directly from a living body, the results vary depending on where and how the sensor is attached and lack reproducibility.

Meanwhile, the system which causes a walker to walk in line with a sound or the like generated in synchronization with a preset walking pace has a problem that as the walker walks at the preset walking pace, biological data such as a pulse may be increased beyond expectation depending on the body burden capacity (physical strength) of the user.

Thus, in view of the above problems of the walking support systems which make supports associated with biological data such as a pulse at the time of walking, it is an object of the present invention to provide a system for estimating biological data at the time of walking which can estimate biological data such as a pulse at the time of walking (exercise) with good reproducibility and a walking pitch generator capable of generating a walking pitch at which desired biological data such as a pulse can be obtained at the time of walking.

SUMMARY OF THE INVENTION

To achieve the above object, a system for estimating biological data at the time of walking, the system comprises: body burden capacity acquiring means; means for acquiring an exercise stress level at the time of walking; and means for estimating biological data at the time of walking; wherein: the body burden capacity acquiring means acquires a relationship between biological data and an exercise stress level prior to walking; the means for acquiring an exercise stress level at the time of walking acquires an exercise stress level at the time of walking; and the means for estimating biological data at the time of walking estimates biological data at the time of walking in correspondence to the exercise stress level acquired by the means for acquiring an exercise stress level at the time of walking based on the relationship acquired by the body burden capacity acquiring means. Thus, signals from a living body are not directly received, and biological data is estimated indirectly by acquiring an exercise stress level which is hardly influenced by where and how the system is attached and the movement of the living body for each walking activity, whereby reproducibility can be improved.

Further, the body burden capacity acquiring means comprises: pre-walking exercise stress level estimating means, and biological data measuring means, wherein: the pre-walking exercise stress level estimating means estimates a number of different exercise stress levels prior to walking, and the biological data measuring means measures biological data corresponding to each of the different exercise stress levels estimated by the pre-walking exercise stress level estimating means. As a result, the relationship between biological data and an exercise stress level prior to walking can be securely determined from at least two points.

Further, the pre-walking exercise stress level estimating means comprises: body weight inputting means, height inputting means, ascending/descending pitch generating means, and means for computing an exercise stress level at the time of ascending or descending a platform, wherein: the body weight inputting means takes in a body weight, the height inputting means takes in the height of the platform, the ascending/descending pitch generating means generates a constant ascending/descending pitch to ascend and descend the platform, and the means for computing an exercise stress level at the time of ascending or descending a platform computes an exercise stress level at the time of ascending or descending the platform based on the body weight inputted by the body weight inputting means, the height of the platform inputted by the height inputting means and the constant ascending/descending pitch generated by the ascending/descending pitch generating means. Thereby, the exercise stress levels prior to walking can be estimated easily by inputting the data and ascending and descending the platform.

Further, the means for acquiring an exercise stress level at the time of walking comprises: walking step measuring means, walking time measuring means, walking pitch computing means, body height inputting means, walking speed computing means, body weight inputting means, and means for computing an exercise stress level at the time of walking, wherein: the walking step measuring means measures walking steps at the time of walking, the walking time measuring means measures walking time during which the walking steps are measured by the walking step measuring means, the walking pitch computing means computes a walking pitch based on the walking steps measured by the walking step measuring means and the walking time measured by the walking time measuring means, the body height inputting means takes in a body height, the walking speed computing means computes a walking speed based on the walking pitch computed by the walking pitch computing means and the body height inputted by the body height inputting means, the body weight inputting means takes in a body weight, and the means for computing an exercise stress level at the time of walking computes an exercise stress level at the time of walking based on the walking speed computed by the walking speed computing means and the body weight inputted by the body weight inputting means. Thus, an exercise stress level which is hardly influenced by where and how the system is attached and the movement of a living body at the time of walking can be determined securely only by inputting and walking.

Further, the system further comprises walking amount computing means for computing a walking amount by use of the biological data estimated by the means for estimating biological data at the time of walking. Thereby, an accurate walking amount based on estimated biological data which is hardly influenced by where and how the system is attached and the movement of a living body can be obtained.

Further, the walking amount is at least one selected from exercise intensity, fat burning efficiency, a fat consumption calorie and an amount of burned fat. Thereby, accurate exercise intensity, accurate fat burning efficiency, an accurate fat consumption calorie or an accurate amount of burned fat based on estimated biological data which is hardly influenced by where and how the system is attached and the movement of a living body can be obtained.

Further, the biological data is a pulse rate. Thus, particularly accurate and easy estimation can be made because the pulse rate is highly correlated with an exercise stress level and shows a significant change with respect to the exercise stress.

Further, to achieve the above object, a walking pitch generator of the present invention comprises: body burden capacity acquiring means, assumed biological data acquiring means, assumed exercise stress level estimating means, body weight inputting means, walking speed computing means, body height inputting means, and walking pitch computing means, wherein: the body burden capacity acquiring means acquires a relationship between biological data and an exercise stress level prior to walking, the assumed biological data acquiring means acquires assumed biological data which represents biological data assumed to be desirably obtained at the time of walking, prior to walking, the assumed exercise stress level estimating means estimates an assumed exercise stress level representing an exercise stress level assumed to be obtained at the time of walking in correspondence to the assumed biological data acquired by the assumed biological data acquiring means based on the relationship acquired by the body burden capacity acquiring means, the body weight inputting means takes in a body weight, the walking speed computing means computes a walking speed based on the body weight inputted by the body weight inputting means and the assumed exercise stress level estimated by the assumed exercise stress level estimating means, the body height inputting means takes in a body height, and the walking pitch computing means computes a walking pitch based on the body height inputted by the body height inputting means and the walking speed computed by the walking speed computing means. Thus, by increasing or decreasing the assumed biological data acquired by the assumed biological data acquiring means, a walking pitch at which desired biological data is obtained at the time of walking can be obtained.

Further, the body burden capacity acquiring means comprises: pre-walking exercise stress level estimating means, and biological data measuring means, wherein: the pre-walking exercise stress level estimating means estimates a number of different exercise stress levels prior to walking, and the biological data measuring means measures biological data corresponding to each of the different exercise stress levels estimated by the pre-walking exercise stress level estimating means. As a result, the relationship between biological data and an exercise stress level prior to walking can be securely determined from at least two points.

Further, the pre-walking exercise stress level estimating means comprises: the body weight inputting means, height inputting means, ascending/descending pitch generating means, and means for computing an exercise stress level at the time of ascending or descending a platform, wherein: the height inputting means takes in the height of the platform, the ascending/descending pitch generating means generates a constant ascending/descending pitch to ascend and descend the platform, and the means for computing an exercise stress level at the time of ascending or descending a platform computes an exercise stress level at the time of ascending or descending the platform based on the body weight inputted by the body weight inputting means, the height of the platform inputted by the height inputting means and the constant ascending/descending pitch generated by the ascending/descending pitch generating means. Thereby, the exercise stress levels prior to walking can be estimated easily by inputting the data and ascending and descending the platform.

Further, the biological data is a pulse rate. Thus, particularly accurate and easy estimation can be made because the pulse rate is highly correlated with an exercise stress level and shows a significant change with respect to the exercise stress.

Further, the assumed biological data acquiring means comprises: exercise intensity inputting means, age inputting means, resting pulse rate acquiring means, and assumed biological data computing means, wherein: the exercise intensity inputting means takes in exercise intensity desired at the time of walking, the age inputting means takes in an age, the resting pulse rate acquiring means acquires a resting pulse rate, and the assumed biological data computing means computes a pulse rate assumed to be desirably obtained at the time of walking based on the exercise intensity inputted by the exercise intensity inputting means, the age inputted by the age inputting means and the resting pulse rate acquired by the resting pulse rate acquiring means. Thus, by increasing or decreasing the exercise intensity inputted by the exercise intensity inputting means, the pulse rate desired at the time of walking can be obtained securely.

Further, the resting pulse rate acquiring means acquires, as the resting pulse rate, a pulse rate corresponding to an exercise stress level of zero based on the relationship acquired by the body burden capacity acquiring means. Thus, the resting pulse rate can be obtained easily from the already acquired relationship between the pulse rate and the exercise stress level.

BRIEF DESCRIPTION OF THE DRAWINGS

FIG. 7 is a physical strength evaluation table which is categorized according to ages and gender.

DETAILED DESCRIPTION OF THE PREFERRED EMBODIMENT

Hereinafter, an embodiment of the present invention will be described with reference to the drawings.

<First Embodiment>

Figure 1:
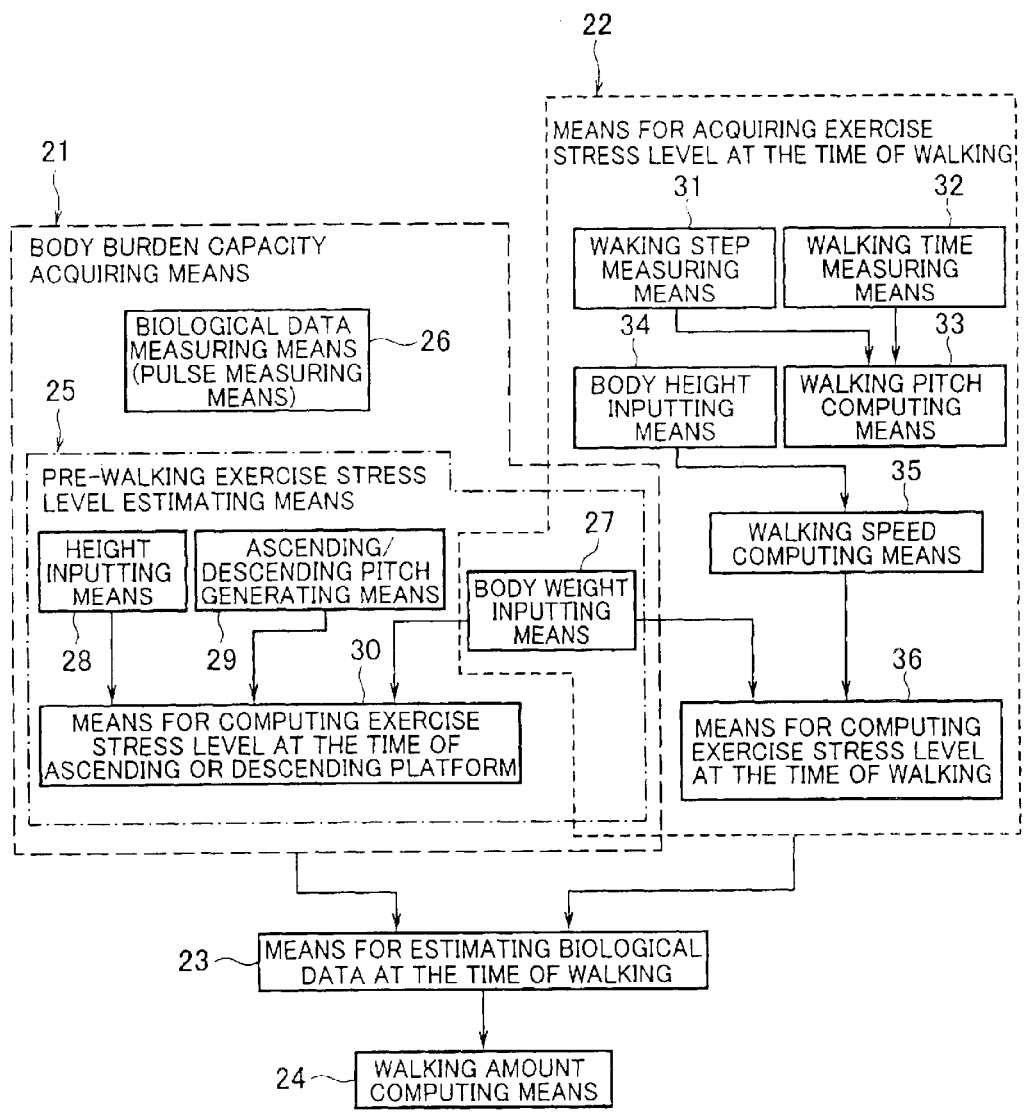
FIG. 1 is a functional block diagram illustrating a functional constitution of a system for estimating biological data at the time of walking according to the present invention.
Figure 2:
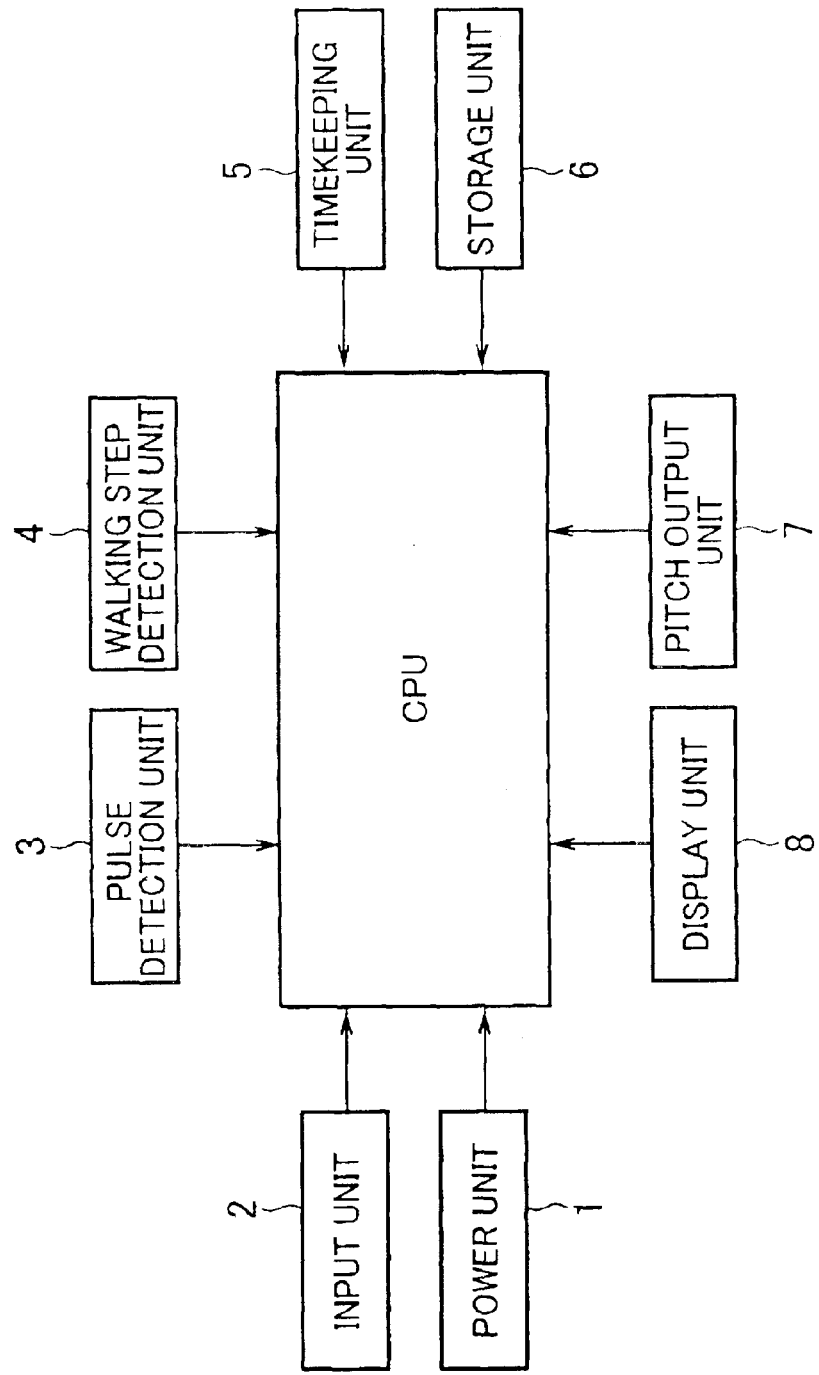
FIG. 2 is a structural block diagram illustrating a structural constitution of the system for estimating biological data at the time of walking or the walking pitch generator according to the present invention.
Figure 3:
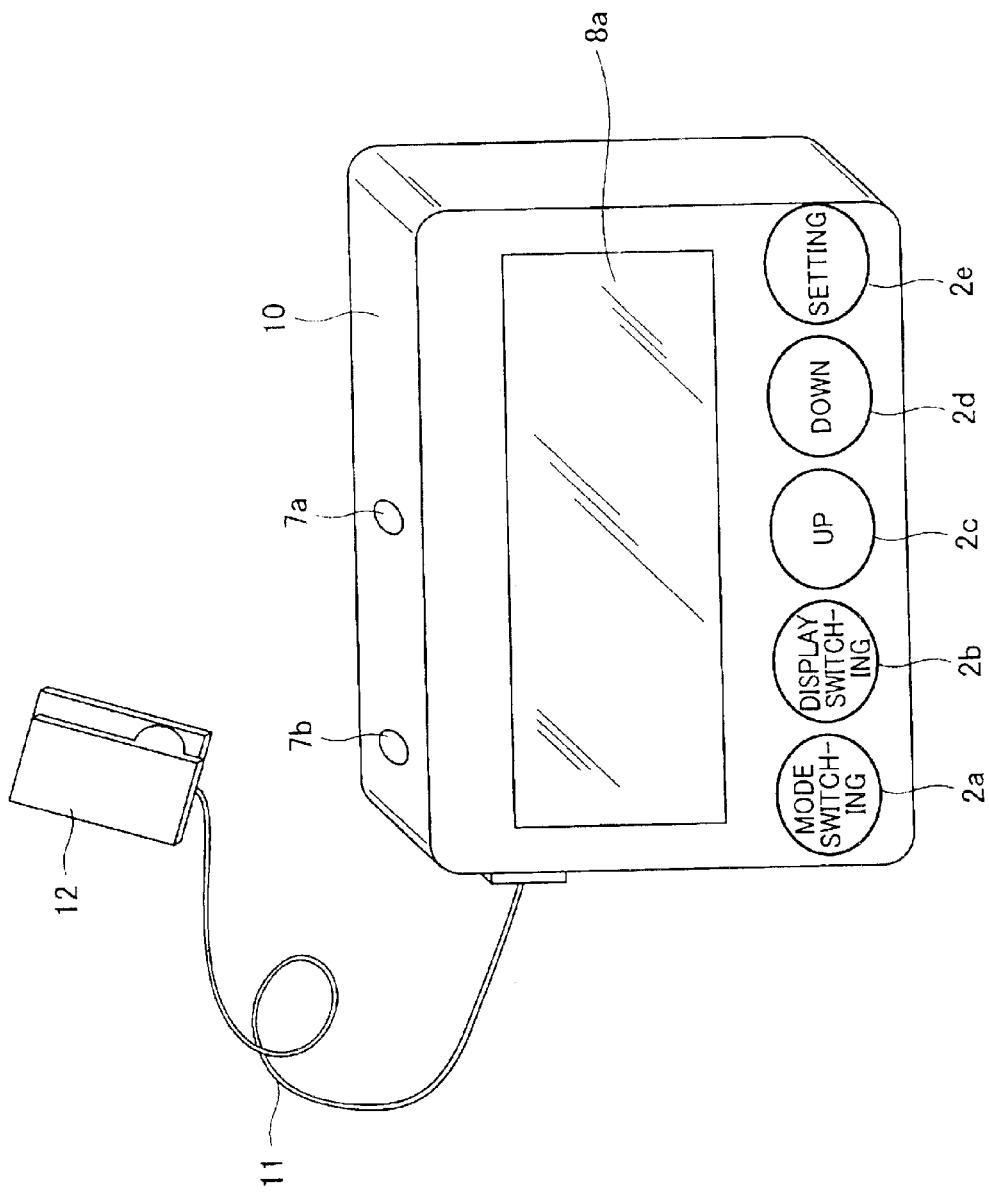
FIG. 3 is an oblique perspective view of the appearance of the system for estimating biological data at the time of walking or the walking pitch generator according to the present invention.

Firstly, the constitution of the system for estimating biological data at the time of walking according to the present invention will be described by use of FIG. 1 which is a functional block diagram illustrating a functional constitution of the system of the present invention, FIG. 2 which is a structural block diagram illustrating a structural constitution of the system, and FIG. 3 which is an oblique perspective view of the appearance of the system. The system for estimating biological data at the time of walking comprises a power unit 1, an input unit 2, a pulse detection unit 3, a walking step detection unit 4, a timekeeping unit 5, a storage unit 6, a pitch output unit 7, a display unit 8 and a CPU (Central Processing Unit) 9. These structural units implement functions of body burden capacity acquiring means 21, means 22 for acquiring an exercise stress level at the time of walking, means 23 for estimating biological data at the time of walking and walking amount computing means 24.

The units constituting the generator will be described in detail.

The power unit 1 supplies power to other units constituting the system. The input unit 2 has 5 key switches, i.e., a mode switching key, a display switching key, an up key, a down key and a setting key, disposed at the exterior front of a case 10, and different actions occur by operations of these keys. The mode switching key 2a switches between a biological data estimating (normal) mode at the time of walking and a physical strength estimating mode. The display switching key 2b switches one display image to another display image. The up key 2c increments a numeric value of an item selected from gender, an age, a body weight, a body height, date, time, the height of a platform, target walking steps and the like. The down key 2d decrements a numeric value of an item selected from gender, an age, a body weight, a body height, date, time, the height of a platform, target walking steps and the like. The setting key 2e performs switching for setting gender, an age, a body weight, a body height, date, time, the height of a platform, target walking steps or the like and sets a numeric value selected by the up key 2c or the down key 2d.

The pulse detection unit 3 comprises a known ear lobule attachable sensor 12 which is connected to the case 10 through a code 11 and detects the pulse data of a person to be measured at the time of ascending or descending a platform. The walking step detection unit 4 comprises a known pendulum type sensor and detects the walking step data of a person to be measured at the time of walking.

The timekeeping unit 5 times a time period, time and other time-related data during ascending or descending a platform or during walking. The storage unit 6 stores various data entered from the input unit 2, various data computed in the CPU 9, and various other data.

The pitch output unit 7 comprises a buzzer 7b and an LED (Light Emitting Diode) 7a and outputs a sound or light as a constant ascending/descending pitch predetermined for ascending or descending a platform. The display unit 8 comprises an LCD (Liquid Crystal Display) which is disposed on an external surface of the case 10 and displays various data entered from the input unit 2, various data computed in the CPU 9, graphs, and other various data.

The CPU 9 computes a pulse rate, walking steps, exercise stress levels at the time of ascending and descending a platform, a walking pitch, a walking speed, an exercise stress level at the time of walking, a pulse rate at the time of walking, exercise intensity, a fat consumption calorie, an amount of burned fat as well as various other output (intermediate and final) data based on various input data from the input unit 2, the pulse detection unit 3, the walking step detection unit 4, the timekeeping unit 5 and the storage unit 6 and controls the operations of these units.

The means constituting functions will be described in detail.

The body burden capacity acquiring means 21 comprises pre-walking exercise stress level estimating means 25 and pulse measuring means 26 and acquires a relationship between a pulse rate and an exercise stress level prior to walking.

The pre-walking exercise stress level estimating means 25 comprises body weight inputting means 27, height inputting means 28, ascending/descending pitch generating means 29 and means 30 for computing an exercise stress level at the time of ascending or descending a platform and estimates a number of different exercise stress levels prior to walking. More specifically, these means constituting the pre-walking exercise stress level estimating means 25 are constituted by the input unit 2, the pitch output unit 7, the timekeeping unit 5, the storage unit 6 and the CPU 9 out of the aforementioned units constituting the generator. The body weight inputting means 27 comprises the input unit 2 and takes in a body weight. The height input means 28 comprises the input unit 2 and takes in the height of a platform. The ascending/descending pitch generating means 29 comprises the storage unit 6, the timekeeping unit 5, the CPU 9 and the pitch output unit 7. The storage unit 6 stores constant ascending/descending pitch data in advance, the timekeeping unit 5 times time, the CPU 9 controls the pitch output unit 7 to generate a constant ascending/descending pitch based on the constant ascending/descending pitch data stored in the storage unit 6 in advance and the time timed in the timekeeping unit 5, and the pitch output unit 7 generates the constant ascending/descending pitch for ascending or descending the platform under the control of the CPU 9. The means 30 for computing an exercise stress level at the time of ascending or descending a platform comprises the CPU 9. The CPU 9 substitutes the body weight and the height of the platform which have been inputted from the input unit 2 and the constant ascending/descending pitch data stored in the storage unit 6 into the following expression (1) so as to compute an exercise stress level before walking (at the time of ascending or descending the platform):

$$Ws = a_1 \times Wt \times Hs \times Ps + a_2 \quad (1)$$

wherein Ws represents an exercise stress level before walking (at the time of ascending or descending the platform), Wt represents a body weight, Hs represents the height of the platform, Ps represents an ascending/descending pitch, and $a_1$ and $a_2$ represent coefficients.

The expression (1) is based on a method comprising multiplying potential energy (mass×acceleration of gravity× height) at the time of ascending or descending the platform by an ascending/descending pitch Ps so as to determine power (pre-walking exercise stress level Ws) by ascending or descending the platform and uses the body weight Wt as the mass of the potential energy (mass×acceleration of gravity×height), the height Hs of the platform as the height of the potential energy, and the coefficients $a_1$ and $a_2$ as combinations of the acceleration of gravity and correction coefficients for changes based on several factors.

The pulse measuring means 26 measures a pulse rate corresponding to each of the different exercise stress levels estimated by the pre-walking exercise stress level estimating means 25. More specifically, the pulse measuring means 26 comprises the pulse detection unit 3 and the CPU 9 out of the aforementioned units constituting the generator. The pulse detection unit 3 detects and digitizes pulse data. The CPU 9 computes a pulse rate based on the pulse data digitized by the pulse detection unit 3.

The means 22 for acquiring an exercise stress level at the time of walking comprises walking step measuring means 31, walking time measuring means 32, walking pitch computing means 33, body height inputting means 34, walking speed computing means 35, body weight inputting means 27 and means 36 for computing an exercise stress level at the time of walking and acquires an exercise stress level at the time of walking.

The walking step measuring means 31 measures walking steps at the time of walking. More specifically, the walking step measuring means 31 comprises the walking step detection unit 4 and the CPU 9 out of the aforementioned units constituting the system. The walking step detection unit 4 detects and digitizes walking step data at the time of walking, and the CPU 9 computes walking steps based on the walking step data digitized in the walking step detection unit 4.

The walking time measuring means 32 measures walking time during which the walking steps are measured by the walking step measuring means 31. More specifically, the walking time measuring means 32 comprises the timekeeping unit 5 out of the aforementioned units constituting the system and measures the time during which the walking step data is detected in the walking step detection unit 4.

The walking pitch computing means 33 computes a walking pitch based on the walking steps measured in the walking step measuring means 31 and the time measured in the walking time measuring means 32. More specifically, the walking pitch computing means 33 comprises the CPU 9 out of the aforementioned units constituting the system and computes the walking pitch by substituting the walking steps at the time of walking which have been computed in the CPU 9 and the walking time measured in the timekeeping unit 5 into the following expression (2):

$$Pw=C/T \tag{2}$$

wherein Pw represents a walking pitch, C represents walking steps, and T represents time.

The body height inputting means 34 comprises the input unit 2 out of the aforementioned units constituting the system and takes in a body height.

The walking speed computing means 35 computes a walking speed based on the walking pitch computed by the walking pitch computing means 33 and the body height inputted by the body height inputting means 34. More specifically, the walking speed computing means 35 comprises the CPU 9 out of the aforementioned units constituting the system and computes the walking speed by substituting the walking pitch computed in the CPU 9 and the body height inputted from the input unit 2 into the following expression (3):

$$Sw=b_1 \times H \times Pw^2 + b_2 \tag{3}$$

wherein Sw represents a walking speed, H represents a body height, Pw represents a walking pitch, and $b_1$ and $b_2$ represent coefficients (correction coefficients for changes based on several factors).

The body weight inputting means 27 is the same as that described with respect to the pre-walking exercise stress level estimating means 25.

The means 36 for computing an exercise stress level at the time of walking computes an exercise stress level at the time of walking based on the walking speed computed by the walking speed computing means 35 and the body weight inputted by the body weight inputting means 27. More specifically, the means 36 for computing an exercise stress level at the time of walking comprises the CPU 9 out of the aforementioned units constituting the system and computes the exercise stress level at the time of walking by substituting the walking speed computed in the CPU 9 and a body weight inputted from the input unit 2 into the following expression (4):

$$Ww=c_1 \times Wt \times Sw^2 + c_2 \tag{4}$$

wherein Ww represents an exercise stress level at the time of walking, Wt represents a body weight, Sw represents a walking speed, and $c_1$ and $c_2$ represent coefficients (correction coefficients for changes based on several factors).

The expression (4) is based on a method of determining kinetic energy (mass×speed$^2$) and uses the body weight Wt as the mass of the kinetic energy (mass×speed$^2$), the walking speed Sw as the speed of the kinetic energy (mass×speed$^2$) and considers the correction coefficients $c_1$ and $c_2$ for changes based on several factors.

Figure 4:
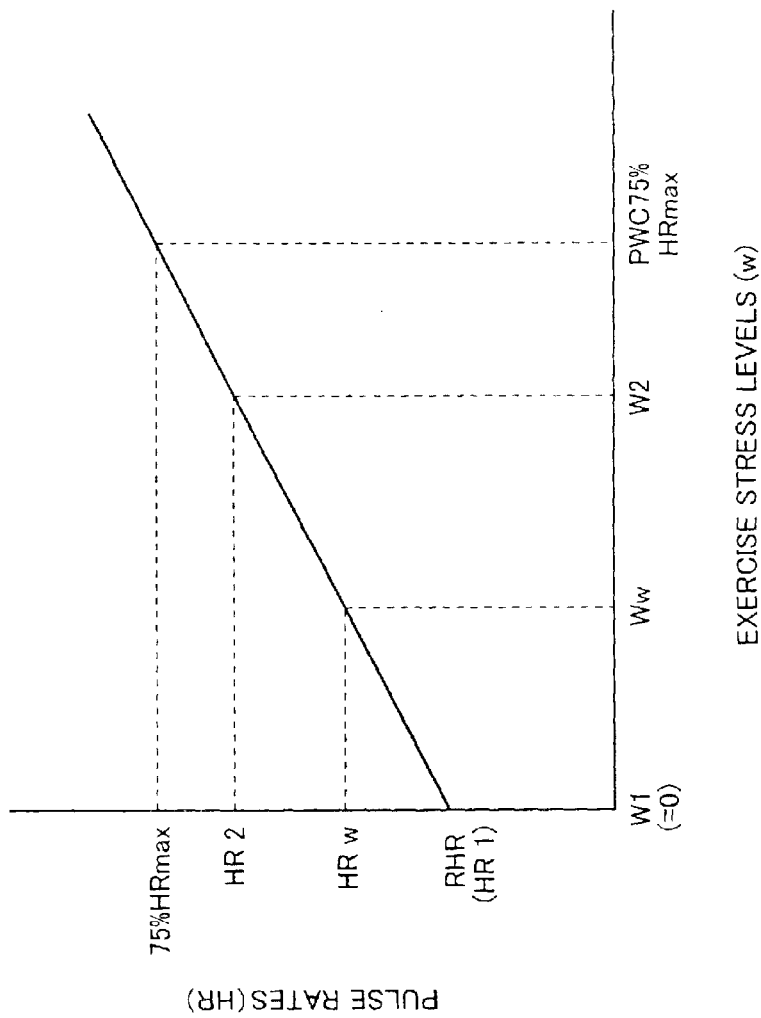
FIG. 4 is a diagram showing a relationship between pulse rates and exercise stress levels.

Means 23 for estimating biological data at the time of walking estimates a pulse rate at the time of walking which corresponds to an exercise stress level at the time of walking which is acquired by the means 22 for acquiring an exercise stress level at the time of walking based on the relationship between pulse rates and exercise stress levels which is acquired by the body burden capacity acquiring means 21. More specifically, the means 23 for estimating biological data at the time of walking comprises the CPU 9 out of the aforementioned units constituting the system and estimates the pulse rate at the time of walking from the exercise stress level at the time of walking and pre-walking exercise stress level computed in the CPU 9 and the pulse rate computed by the pulse measuring means 26. For example, as shown in FIG. 4 which shows the relationship between pulse rates and exercise stress levels, when pre-walking exercise stress levels which are computed by the means 30 for computing an exercise stress level at the time of ascending or descending a platform are W1 and W2, pulse rates measured by the pulse measuring means 26 in correspondence to the pre-walking exercise stress levels are HR1 and HR2, and the exercise stress level at the time of walking computed by the means 36 for computing an exercise stress level at the time of walking is Ww, a pulse rate at the time of walking is computed by substituting these data into the following expression (5):

$$HRw=(HR2-HR1) \times Ww/(W2-W1)+HR1 \tag{5}$$

wherein HRw represents a pulse rate at the time of walking, Ww represents an exercise stress level at the time of walking, W1 represents a first exercise stress level before walking, W2 represents a second exercise stress level before walking, HR1 represents a pulse rate corresponding to W1, and HR2 represents a pulse rate corresponding to W2.

Walking amount computing means 24 computes exercise intensity, fat burning efficiency, a fat consumption calorie and an amount of burned fat by use of the pulse rate at the time of walking estimated by the means 23 for estimating biological data at the time of walking. More specifically, the walking amount computing means 24 comprises the CPU 9, the input unit 2 and the timekeeping unit 5 out of the aforementioned units constituting the system. The CPU 9 estimates a resting pulse rate RHR (which in FIG. 4 corresponds to the pre-walking pulse rate HR1 corresponding to the first exercise stress level W1 before walking corresponding to an exercise stress level of 0w) from the already acquired relationship between pulse rates and exercise stress levels and then substitutes the resting pulse rate RHR (HR1), the already computed pulse rate at the time of walking, and the age inputted from the input unit 2 into the following expression (6) so as to compute exercise intensity at the time of walking:

$$Ms=(HRw-RHR)/(220-A-RHR)\times 100 \qquad (6)$$

wherein Ms represents exercise intensity, HRw represents a pulse rate at the time of walking, RHR represents a resting pulse rate, and A represents an age.

Further, the CPU 9 further computes fat burning efficiency at the time of walking by substituting the computed exercise intensity, the walking time measured by the timekeeping unit 5 and the gender, body weight and body height inputted from the input unit 2 into the following expression (7):

$$Fbe=-0.41771\times Ms-0.37521\times RHR+0.585518\times T-9.34669\times Se+1.896506\times BMI+20.83170 \qquad (7)$$

wherein Fbe represents fat burning efficiency, Ms represents exercise intensity, RHR represents a resting pulse rate, T represents time, Se represents gender, and BMI represents a body-mass index (=body weight×body height$^2$).

Further, the CPU 9 further computes a fat consumption calorie by substituting the computed fat burning efficiency, the exercise stress level at the time of walking and a basal metabolic level into the following expression (8). The basal metabolic level is computed based on the gender, age and body weight inputted from the input unit 2 and a known basal metabolism reference value stored in the storage unit 6:

$$Fk=0.014\times Ww\times Bm\times Fbe/100 \qquad (8)$$

wherein Fk represents a fat consumption calorie, Ww represents an exercise stress level at the time of walking, Bm represents a basal metabolic level, and Fbe represents fat burning efficiency.

The computation portion 0.014×Ww in the expression (8) represents a calorie consumed by walking.

Further, the CPU 9 further computes an amount of burned fat by substituting the computed fat consumption calorie into the following expression (9) taking a calorie per g of fat of 9 kcal and a proportion of pure fat in a fat tissue of 80% into consideration:

$$Fbm=Fk/9\times 0.8 \qquad (9)$$

wherein Fbm represents an amount of burned fat, and Fk represents a fat consumption calorie.

Figure 5:
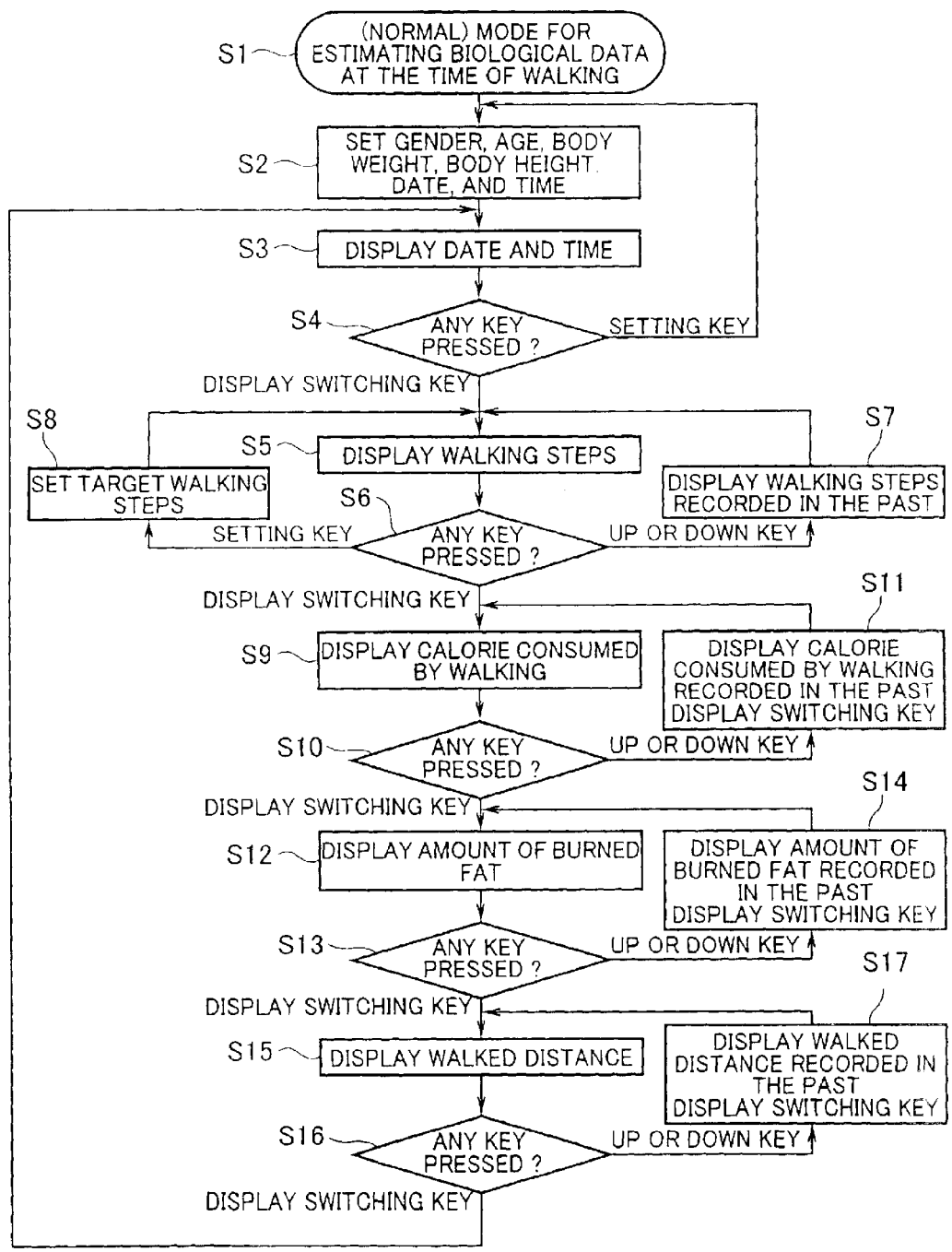
FIG. 5 is a flowchart illustrating procedural steps in a biological data estimating (normal) mode at the time of walking.
Figure 6:
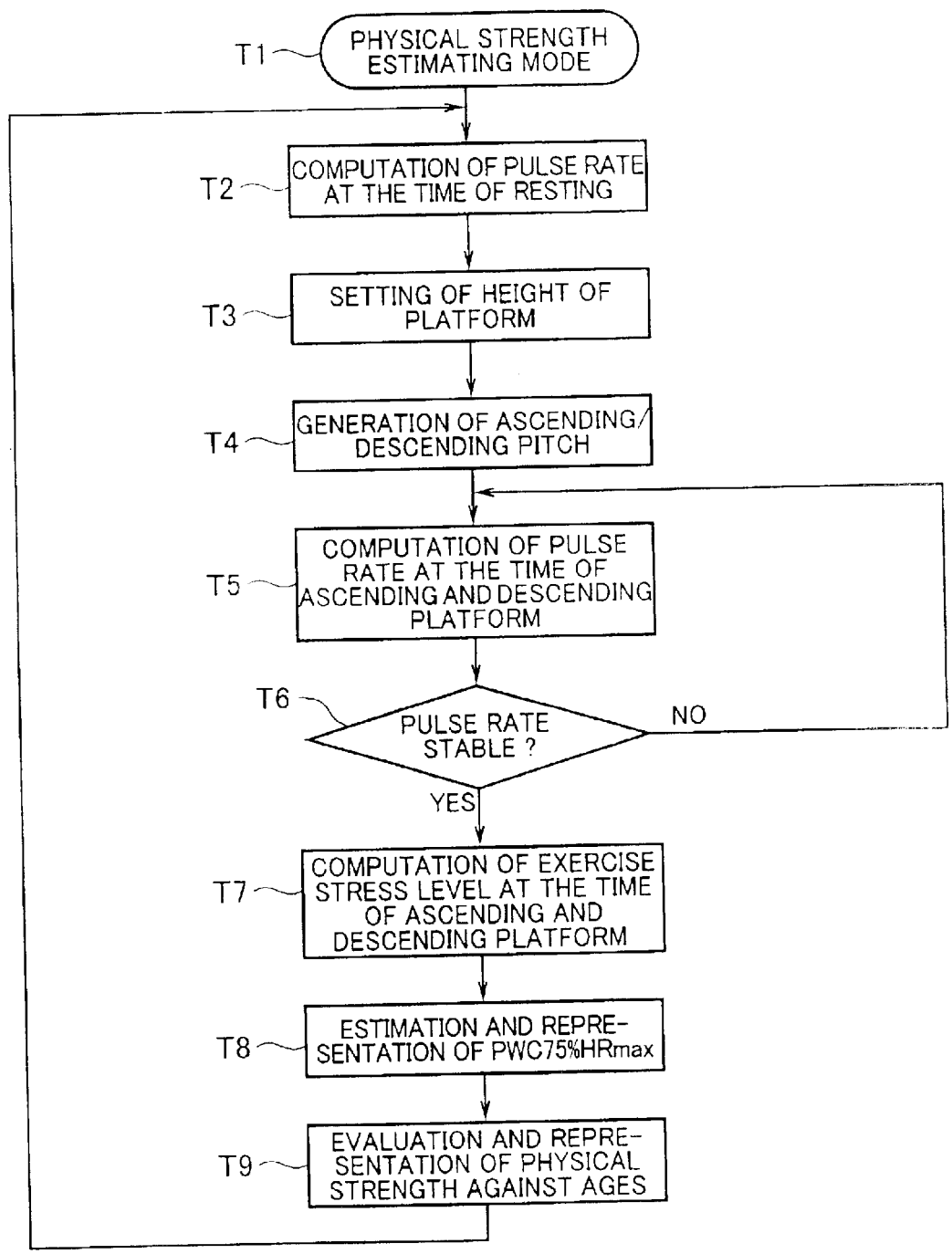
FIG. 6 is a flowchart illustrating procedural steps in a physical strength estimating mode.

Next, the operations and actions of the system for estimating biological data at the time of walking according to the present invention will be described by use of FIG. 5 which is a flowchart showing procedural steps in a (normal) mode for estimating biological data at the time of walking of the system according to the present invention and FIG. 6 which is a flowchart showing procedural steps in a physical strength estimating mode. In the above constitution of the present invention, the system of the present invention is capable of not only estimating a pulse rate at the time of walking (exercise) and determining a walking amount by use of the estimated pulse rate but also estimating physical strength (endurance). These features will also be described hereinafter.

Firstly, the procedural steps in the biological data estimating (normal) mode at the time of walking will be described in detail by use of FIG. 5.

Firstly, by setting a battery as a power source in the power unit 1, power is supplied to the units (STEP S1).

Subsequently, display images for initialization of gender, an age, a body weight, a body height, date and time will be displayed. At this point, gender, an age, a body weight, a body height, date and time are set in the order presented by switching and selecting numeric values or characters by means of the up key 2c or the down key 2d and setting the selected numeric value or characters by means of the setting key 2e (STEP S2).

Then, after completion of the initialization in STEP S2, the timekeeping unit 5 starts timing of time and the walking step detection unit 4 starts detection of walking step data. Then, in the CPU 9, the following various processes are performed based on the various data initialized in STEP S2, and the current date and time will be displayed on the display unit 8 (LCD 8a) (STEP S3).

As the various computations to be performed in the CPU 9, firstly, walking steps are computed based on the walking step data detected by the walking step detection unit 4, and the computed walking steps and the time timed by the timekeeping unit 5 are substituted into the expression (2) so as to compute a walking pitch. Then, the computed walking pitch and the body height inputted from the input unit 2 are substituted into the expression (3) so as to compute a walking speed. Then, the computed walking speed and the time timed by the timekeeping unit 5 are substituted into the following expression (10) so as to compute a walked distance:

$$D=Sw\times T \qquad (10)$$

wherein D represents a walked distance, Sw represents a walking speed, and T represents time.

Then, the computed walking speed and the body weight inputted from the input unit 2 are substituted into the expression (4) so as to compute an exercise stress level at the time of walking. Then, the age inputted from the input unit 2 is substituted into the following expression (11) so as to compute 75% HRmax (pulse rate corresponding to 75% of maximum pulse rate):

$$E=(220-A)\times 0.75 \qquad (11)$$

wherein E represents 75% HRmax, and A represents an age.

Then, if processes in steps in the physical strength estimating mode to be described later are not performed, the exercise stress level at the time of walking and 75% HRmax computed in the CPU 9, the resting pulse rate and PWC75% HRmax (exercise stress level at the pulse rate corresponding to 75% of maximum pulse rate) stored in the storage unit 6 are substituted into the following expression (12) so as to compute a pulse rate at the time of walking:

$$HRw=(E-RHR)\times Ww/PWC+RHR \qquad (12)$$

wherein HRw represents a pulse rate at the time of walking (before measurement of physical strength), E represents 75% HRmax, Ww represents an exercise stress level at the time of walking, PWC represents PWC75% HRmax (specified value), and RHR represents a resting pulse rate (specified value).

Meanwhile, if the processes in the steps in the physical strength estimating mode to be described later are performed, the exercise stress level at the time of walking and two different pre-walking exercise stress levels (first exercise stress level and second exercise stress level) computed in the CPU 9 and two pre-walking pulse rates corresponding to these exercise stress levels (pre-walking pulse rate corresponding to the first exercise stress level and pre-walking pulse rate corresponding to the second exercise stress level) are substituted into the expression (5) so as to compute a pulse rate at the time of walking.

Then, if processes in steps in the physical strength estimating mode to be described later are not performed, the pulse rate at the time of walking computed in the CPU 9, the age inputted from the input unit 2 and the resting pulse rate (specified value) stored in the storage unit 6 are substituted into the expression (6) so as to compute exercise intensity. Meanwhile, if the processes in the steps in the physical strength estimating mode to be described later are performed, the computed pulse rate at the time of walking, the age inputted from the input unit 2 and the resting pulse rate based on the relationship between pulse rates and exercise stress levels before walking are substituted into the expression (6) so as to compute exercise intensity.

Then, the computed exercise intensity, the time measured by the timekeeping unit 5 and the gender, body weight and body height inputted from the input unit 2 are substituted into the expression (7) so as to compute fat burning efficiency. Then, the computed fat burning efficiency, the exercise stress level at the time of walking and a basal metabolic level are substituted into the expression (8) so as to compute a fat consumption calorie. Further, when the fat consumption calorie is computed, a calorie consumed by walking alone is also computed. Then, the computed fat consumption calorie is substituted into the expression (9) so as to compute an amount of burned fat.

Then, if the setting key 2e is pressed with the date and time displayed on the display unit 8 (setting key in STEP S4), STEP S2 is repeated. Meanwhile, if the display switching key 2b is pressed with the date and time displayed on the display unit 8 (display switching key in STEP S4), walking steps after the start of detection of the walking steps is displayed on the display unit 8 (STEP S5). The date and time are kept displayed on the display unit 8 until the display switching key 2b or the setting key 2e is pressed.

Then, if the up key 2c or the down key 2d is pressed with the walking steps displayed on the display unit 8 (up or down key in STEP S6), past walking steps are displayed (STEP S7). More specifically, each time the down key 2d is pressed down, walking steps of the previous day are displayed, and after dating back to one week ago, a total of the last one week is displayed, and then the current (today's) walking steps in STEP S5 are displayed again. As for the up key 2c, the series of display switchings for the down key 2d are reversed.

Further, if the setting key 2e is pressed with the walking steps displayed on the display unit 8 (setting key in STEP S6), the displayed screen image is switched to a screen image for setting target walking steps or a screen image for comparing with set target walking steps (STEP S8). More specifically, if target walking steps per day have not been set in the past, a screen image for setting the target walking steps will be displayed. After the target walking steps per day are set by switching from one numeric value to another and selecting a numeric value by means of the up key 2c or the down key 2d and setting the selected numeric value by means of the setting key 2e, STEP S5 where the current (today's) walking steps are displayed is carried out again. Meanwhile, if the target walking steps per day have already been set in the past, an achievement ratio of the current (today's) walking steps to the target walking steps per day or a graph illustrating the achievement ratio is displayed as a screen image for comparing with the target walking steps per day. At the press of the setting key 2e, STEP P6 where the current (today's) walking steps are displayed is carried out again.

Meanwhile, if the display switching key 2b is pressed with the walking steps displayed on the display unit 8 (display switching key in STEP S6), the calorie consumed by walking is displayed on the display unit 8 (STEP S9). The walking steps are kept displayed on the display unit 8 until the up key 2c, the down key 2d, the setting key 2e or the display switching key 2b is pressed.

Then, if the up key 2c or the down key 2d is pressed with the calorie consumed by walking displayed on the display unit 8 (up or down key in STEP S10), a calorie consumed by walking which has been recorded in the past is displayed (STEP S11). More specifically, each time the down key 2d is pressed, the calorie consumed by walking on the previous day is displayed, and after dating back to one week ago, a total of the last one week is displayed, and the calorie consumed by the current (today's) walking in STEP S9 is displayed again. As for the up key 2c, the series of display switchings for the down key 2d are reversed.

Meanwhile, if the display switching key 2b is pressed with the calorie consumed by walking displayed on the display unit 8 (display switching key in STEP S10), the amount of burned fat is displayed on the display unit 8 (STEP S12). The calorie consumed by walking is kept displayed on the display unit 8 until the up key 2c, the down key 2d, the setting key 2e or the display switching key 2b is pressed.

Then, if the up key 2c or the down key 2d is pressed with the amount of burned fat displayed on the display unit 8 (up or down key in STEP S13), an amount of burned fat recorded in the past is displayed (STEP S14). More specifically, each time the down key 2d is pressed, the amount of burned fat on the previous day is displayed, and after dating back to one week ago, a total of the last one week is displayed, and then the current (today's) amount of burned fat in STEP S12 is displayed again. As for the up key 2c, the series of display switchings for the down key 2d are reversed.

Meanwhile, if the display switching key 2b is pressed with the amount of burned fat displayed on the display unit 8 (display switching key in STEP S13), the walked distance is displayed on the display unit 8 (STEP S15). The amount of burned fat is kept displayed on the display unit 8 until the up key 2c, the down key 2d or the display switching key 2b is pressed.

Then, if the up key 2c or the down key 2d is pressed with the walked distance displayed on the display unit 8 (up or down key in STEP S16), a walked distance recorded in the past is displayed (STEP S17). More specifically, each time the down key 2d is pressed, the walked distance on the previous day is displayed, and after dating back to one week ago, a total of the last one week is displayed, and then the current (today's) walked distance in STEP S15 is displayed again. As for the up key 2c, the series of display switchings for the down key 2d are reversed.

Meanwhile, if the display switching key 2b is pressed with the walked distance displayed on the display unit 8 (display switching key in STEP S16), STEP S3 where the current date and time are displayed is carried out again, and the subsequent steps are also carried out again. The walked distance is kept displayed on the display unit 8 until the up key 2c, the down key 2d or the display switching key 2b is pressed.

Next, the procedural steps in the physical strength estimating mode will be described in detail by use of FIG. 6.

At the press of the mode switching key 2a in any of the foregoing steps subsequent to STEP P3 in the biological data estimating (normal) mode at the time of walking, the walking (normal) mode is switched to the physical strength estimating mode (STEP T1).

Subsequently, a pulse rate is displayed on the display unit 8. Then, a user in a resting state (indicating an exercise stress level of 0) attaches the ear lobule attachable sensor 12 to his ear lobule. Thereby, pulse data at the time of resting (i.e., when an exercise stress level is 0) is detected in the pulse detection unit 3, and a pulse rate at the time of resting (i.e., when an exercise stress level is 0) is computed in the CPU 9 (STEP T2). This pulse rate at the time of resting (i.e., when an exercise stress level is 0) corresponds to the pre-walking pulse rate corresponding to the first exercise stress level (exercise stress level=0).

Then, a screen image for setting the height of a platform is displayed on the display unit 8. Then, the height of the platform is set by switching from one numeric value to another and selecting a numeric value by means of the up key 2c or the down key 2d and setting the selected numeric value by means of the setting key 2e (STEP T3).

Then, a constant ascending/descending pitch (e.g., 100 times/min) predetermined for ascending or descending the platform is outputted from the pitch output unit 7 (STEP T4).

Subsequently, the user ascends and descends the platform whose height has been set by the input unit 2 in synchronization with the constant ascending/descending pitch outputted from the pitch output unit 7. Thereby, pulse data while the user is ascending and descending the platform is detected in the pulse detection unit 3, and a pulse rate at the time of ascending and descending the platform is computed in the CPU 9 (STEP T5). This pulse rate at the time of ascending and descending the platform corresponds to the pre-walking pulse rate corresponding to the second exercise stress level.

Then, it is determined whether the pulse rate computed in the CPU 9 is stable within a given range (STEP T6). If the pulse rate is not stable (NO in STEP T6), STEP T5 is carried out again. Meanwhile, if the pulse rate is stable (YES in STEP T6), the body weight and the height of the platform which have been inputted from the input unit 2 and the constant ascending/descending pitch data stored in the storage unit 6 are substituted into the expression (1) so as to compute an exercise stress level at the time of ascending and descending the platform (STEP T7).

Then, the pulse rate at the time of resting (i.e., when an exercise stress level is 0) which has been computed by the CPU 9 in STEP T2, the pulse rate at the time of ascending and descending the platform which has been determined stable by the CPU in STEP T6, and the exercise stress level at the time of ascending and descending the platform which has been computed in STEP T7 are substituted into the following expression (13) which has been pre-stored in the storage unit 6, so as to compute PWC75% HRmax (STEP T8):

$$PWC = Ws \times (E - RHR)/HR - RHR \qquad (13)$$

wherein PWC represents PWC75% HRmax, Ws represents an exercise stress level at the time of ascending and descending the platform, E represents 75% HRmax, HR represents a pulse rate at the time of ascending and descending the platform, and RHR represents a pulse rate at the time of resting (i.e., when an exercise stress level is 0).

Then, the CPU 9 refers to a physical strength evaluation table as shown in FIG. 7 which is categorized according to gender and ages and stored in the storage unit 6 in advance, specifies an evaluation comment corresponding to the gender and age inputted from the input unit 2 and the PWC75% HRmax which has been computed in the CPU 9 (STEP T9), and then returns to STEP T2 to measure a resting pulse rate. These steps are repeated until the mode switching key 2a is pressed again.

For one thing, as described above, the system for estimating biological data at the time of walking of the present invention can estimate a pre-walking exercise stress level easily by inputting a body weight and the height of a platform from the body weight inputting means 27 and the height inputting means 28 and causing a user to ascend and descend the platform in synchronization with a constant ascending/descending pitch generated from the ascending/descending pitch generating means 29.

For another thing, the walking pitch generator of the present invention can securely obtain a relationship between biological data and exercise stress levels prior to walking from at least two points by obtaining a number of different pre-walking exercise stress levels and measuring biological data corresponding to each of these exercise stress levels by the biological data measuring means 26.

For another thing, the system of the present invention can securely obtain an exercise stress level which is hardly influenced by where and how the system is attached and the movement of the living body at the time of walking by going through computation steps such as the walking pitch computing means 33, the walking speed computing means 35 and the means 36 for computing an exercise stress level at the time of walking based on a body height inputted from the body height inputting means 34, walking steps at the time of walking measured by the walking step measuring means 31 and time at the time of walking measured by the walking time measuring means 32.

For another thing, biological data at the time of walking is estimated by the means 23 for estimating biological data at the time of walking based on the acquired relationship between biological data and exercise stress levels before walking and the acquired exercise stress level at the time of walking. Thus, biological data is estimated indirectly for each walking activity, whereby reproducibility can be improved.

For another thing, since a walking amount representing exercise intensity, fat burning efficiency, a fat consumption calorie or an amount of burned fat is computed by the walking amount computing means 24 based on the biological data at the time of walking which is hardly influenced by where and how the system is attached and the movement of the living body, an accurate value can be obtained.

In the above embodiment, the user is caused to ascend and descend the platform so as to obtain the relationship between biological data and exercise stress levels. The relationship can also be obtained by causing a user to keep walking at a constant pace or run a certain distance.

Further, although a pulse rate has been presented as an example of biological data, any other biological data which changes by walking activity such as a blood pressure may also be used.

Further, in addition to exercise intensity, fat burning efficiency, a fat consumption calorie and an amount of burned fat, the walking amount computing means 24 may also obtain a value which includes at least biological data the time of walking and changes by walking as a walking amount.

In the description of the present invention, walking is a concept including running, and a pulse is a concept including a heart beat.

As described above, according to the present invention, since biological data at the time of walking is estimated indirectly by relating an exercise stress level which has been acquired at the time of walking in the means for acquiring an exercise stress level at the time of walking and which is hardly influenced by where and how the system is attached and the movement of a living body to a relationship between biological data and exercise stress levels which has been acquired before walking in the body burden capacity acquiring means, reproducibility can be improved, and a reliable result can always be obtained.

Further, the relationship between biological data and exercise stress levels before walking can be obtained securely because biological data corresponding to a number of different exercise stress levels estimated by the pre-walking exercise stress level estimating means are measured by the biological data measuring means.

Further, in the pre-walking exercise stress level estimating means, a pre-walking exercise stress level can be estimated easily by inputting a body weight and the height of a platform from the body weight inputting means and the height inputting means, respectively, and causing a user to perform a simple task, i.e., ascend and descend the platform in synchronization with a constant ascending/descending pitch generated from the ascending/descending pitch generating means.

Further, the means for acquiring an exercise stress level at the time of walking can securely obtain an exercise stress level which is hardly influenced by where and how the system is attached and the movement of a living body at the time of walking by inputting a body height from the body height inputting means, measuring walking steps by the walking step measuring means, measuring walking time by the walking time measuring means, and going through computation steps such as the walking pitch computing means, the walking speed computing means and the means for computing an exercise stress level at the time of walking.

Further, since a walking amount representing exercise intensity, fat burning efficiency, a fat consumption calorie or an amount of burned fat is computed by the walking amount computing means based on the biological data at the time of walking which is hardly influenced by where and how the system is attached and the movement of the living body, an accurate value can be obtained.

Further, by use of a pulse rate which is highly related to an exercise stress level and exhibits a significant change with respect to an exercise stress as biological data, particularly accurate and easy estimation can be made.

<Second Embodiment>

Figure 8:
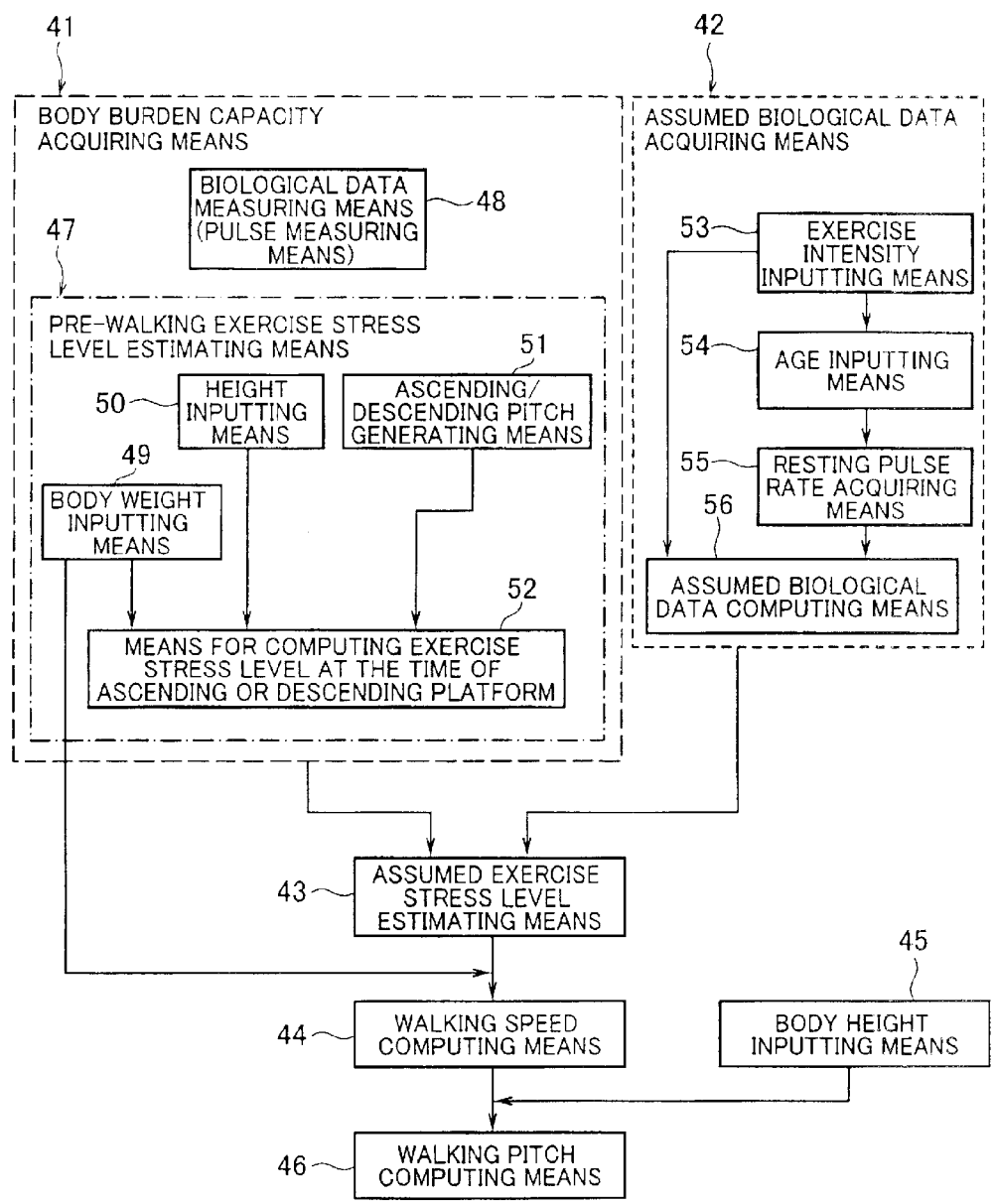
FIG. 8 is a functional block diagram illustrating a functional constitution of a walking pitch generator according to the present invention.

Next, the constitution of the walking pitch generator according to the present invention will be described by use of FIG. 8 which is a functional block diagram illustrating a functional constitution of the walking pitch generator of the present invention, FIG. 2 which is a structural block diagram illustrating a structural constitution of the generator, and FIG. 3 which is an oblique perspective view of the appearance of the generator. The walking pitch generator comprises a power unit 1, an input unit 2, a pulse detection unit 3, a walking step detection unit 4, a timekeeping unit 5, a storage unit 6, a pitch output unit 7, a display unit 8 and a CPU (Central Processing Unit) 9. These structural units implement functions of body burden capacity acquiring means 41, assumed biological data acquiring means 42, assumed exercise stress level estimating means 43, walking speed computing means 44, body height inputting means 45, and walking pitch computing means 46.

The units constituting the generator will be described in detail.

The power unit 1 supplies power to other units constituting the system. The input unit 2 has 5 key switches, i.e., a mode switching key, a display switching key, an up key, a down key and a setting key, disposed at the exterior front of a case 10, and different actions occur by operations of these keys. The mode switching key 2a switches between a walking (normal) mode and a physical strength estimating mode. The display switching key 2b switches one display image to another display image. The up key 2c increments a numeric value of an item selected from gender, an age, a body weight, a body height, date, time, the height of a platform, exercise intensity, target walking steps and the like. The down key 2d decrements a numeric value of an item selected from gender, an age, a body weight, a body height, date, time, the height of a platform, exercise intensity, target walking steps and the like. The setting key 2e performs switching for setting gender, an age, a body weight, a body height, date, time, the height of a platform, exercise intensity, target walking steps or the like and sets a numeric value selected by the up key 2c or the down key 2d.

The pulse detection unit 3 comprises a known ear lobule attachable sensor 12 which is connected to the case 10 through a code 11 and detects the pulse data of an user at the time of ascending o descending a platform. The walking step detection unit 4 comprises a known pendulum type sensor and detects the walking step data of an user at the time of walking.

The timekeeping unit 5 times a time period, time and other time-related data during ascending or descending a platform or during walking. The storage unit 6 stores various data entered from the input unit 2, various data computed in the CPU 9, and various other data.

The pitch output unit 7 comprises a buzzer 7b and an LED (Light Emitting Diode) 7a and outputs a sound or light as a constant ascending/descending pitch predetermined for ascending or descending a platform or as a walking pitch for walking. The display unit 8 comprises an LCD (Liquid Crystal Display) 8a which is disposed on an external surface of the case 10 and displays various data entered from the input unit 2, various data computed in the CPU 9, graphs, and other various data.

The CPU 9 computes a pulse rate, walking steps, exercise stress levels at the time of ascending and descending a platform, an assumed pulse rate (assumed biological data), an assumed exercise stress level, a walking speed, a walking pitch as well as various other output (intermediate and final) data based on various input data from the input unit 2, the pulse detection unit 3, the walking step detection unit 4, the timekeeping unit 5 and the storage unit 6 and controls the operations of these units.

The means constituting functions will be described in detail.

The body burden capacity acquiring means 41 comprises pre-walking exercise stress level estimating means 47 and pulse measuring means 48 and acquires a relationship between a pulse rate and an exercise stress level prior to walking.

The pre-walking exercise stress level estimating means 47 comprises body weight inputting means 49, height inputting means 50, ascending/descending pitch generating means 51 and means 52 for computing an exercise stress level at the time of ascending or descending a platform and estimates a number of different exercise stress levels prior to walking. More specifically, these means constituting the pre-walking exercise stress level estimating means 47 are constituted by the input unit 2, the pitch output unit 7, the timekeeping unit 5, the storage unit 6 and the CPU 9 out of the aforementioned units constituting the generator. The body weight inputting means 49 comprises the input unit 2 and takes in a body weight. The height input means 50 comprises the input unit 2 and takes in the height of a platform. The ascending/descending pitch generating means 51 comprises the storage unit 6, the timekeeping unit 5, the CPU 9 and the pitch output unit 7. The storage unit 6 stores constant ascending/descending pitch data in advance, the timekeeping unit 5 times time, the CPU 9 controls the pitch output unit 7 to generate a constant ascending/descending pitch based on the constant ascending/descending pitch data stored in the storage unit 6 in advance and the time timed in the timekeeping unit 5, and the pitch output unit 7 generates the constant ascending/descending pitch for ascending or descending the platform under the control of the CPU 9. The means 52 for computing an exercise stress level at the time of ascending or descending a platform comprises the CPU 9. The CPU 9 substitutes the body weight and the height of the platform which have been inputted by the input unit 2 and the constant ascending/descending pitch data stored in the storage unit 6 into the following expression (1) so as to compute an exercise stress level before walking (at the time of ascending or descending the platform):

$$Ws = a_1 \times Wt \times Hs \times Ps + a_2 \qquad (1)$$

wherein Ws represents an exercise stress level before walking (at the time of ascending or descending the platform), Wt represents a body weight, Hs represents the height of the platform, Ps represents an ascending/descending pitch, and $a_1$ and $a_2$ represent coefficients.

The expression (1) is based on a method comprising multiplying potential energy (mass×acceleration of gravity× height) at the time of ascending or descending the platform by an ascending/descending pitch Ps so as to determine power (pre-walking exercise stress level Ws) by ascending or descending the platform and uses the body weight Wt as the mass of the potential energy (mass×acceleration of gravity×height), the height Hs of the platform as the height of the potential energy, and the coefficients $a_1$ and $a_2$ as combinations of the acceleration of gravity and correction coefficients for changes based on several factors.

The pulse measuring means 48 measures a pulse rate corresponding to each of the different exercise stress levels estimated by the pre-walking exercise stress level estimating means 47. More specifically, the pulse measuring means 48 comprises the pulse detection unit 3 and the CPU 9 out of the aforementioned units constituting the generator. The pulse detection unit 3 detects and digitizes pulse data. The CPU 9 computes a pulse rate based on the pulse data digitized by the pulse detection unit 3.

The assumed biological data acquiring means 42 comprises exercise intensity inputting means 53, age inputting means 54, resting pulse rate acquiring means 55 and assumed biological data computing means 56 and acquires a pulse rate assumed to be desirably obtained at the time of walking (hereinafter referred to as "assumed pulse rate").

The exercise intensity inputting means 53 comprises the input unit 2 out of the aforementioned units constituting the generator and takes in exercise intensity. The age inputting means 54 comprises the input unit 2 out of the aforementioned units constituting the generator and takes in an age.

The resting pulse rate acquiring means 55 comprises the CPU 9 out of the aforementioned units constituting the generator and estimates a resting pulse rate (pulse rate corresponding to an exercise stress level of 0 w) based on the relationship between pulse rates and exercise stress levels which has been acquired by the body burden capacity acquiring means 41 (that is, the plurality of different exercise stress levels before walking (at the time of ascending or descending the platform) and the pulse rates corresponding to these exercise stress levels, all of which have been computed by the CPU).

The assumed biological data computing means 56 computes an assumed pulse rate based on the exercise intensity inputted by the exercise intensity inputting means 53, the age inputted by the age inputting means 54, and the resting pulse rate estimated by the resting pulse rate acquiring means 55. More specifically, the assumed biological data computing means 56 comprises the CPU 9 out of the aforementioned units constituting the generator and computes the assumed pulse rate by substituting the resting pulse rate computed by the CPU 9 and the exercise intensity and age inputted from the input unit 2 into the following expression (2):

$$HRh = Ms/100 \times (220 - A - RHR) + RHR \qquad (2)$$

wherein HRh represents an assumed pulse rate, Ms represents exercise intensity, A represents an age, and RHR represents a resting pulse rate.

The assumed exercise stress level estimating means 43 estimates an exercise stress level (hereinafter referred to as "assumed exercise stress level") assumed to be obtained at the time of walking in correspondence to the assumed pulse rate acquired by the assumed biological data acquiring means 56 based on the relationship acquired by the body burden capacity acquiring means 41. More specifically, the assumed exercise stress level estimating means 43 comprises the CPU 9 out of the aforementioned units constituting the generator and estimates the assumed exercise stress level based on the different exercise stress levels before walking (at the time of ascending or descending the platform) which have been computed in the CPU 9, the pulse rates corresponding to the different exercise stress levels, and the assumed pulse rate. For example, as in FIG. 4 which shows the relationship between pulse rates and exercise stress levels, when the different exercise stress levels before walking which are computed by the means 52 for computing an exercise stress level at the time of ascending or descending the platform are W1 and W2, pulse rates measured by the pulse measuring means 48 in correspondence to the exercise stress levels W1 and W2 before walking are HR1 and HR2, and the assumed pulse rate acquired by the assumed biological data acquiring means 42 is HRh, an assumed exercise stress level is computed and estimated by substituting these data into the following expression (3):

$$Wh = (HRh - HR1) \times (W2 - W1)/(HR2 - HR1) \qquad (3)$$

wherein Wh represents an assumed exercise stress level, HRh represents an assumed pulse rate, W1 represents a first exercise stress level before walking, W2 represents a second exercise stress level before walking, HR1 represents a pulse rate corresponding to W1, and HR2 represents a pulse rate corresponding to W2.

The walking speed computing means 44 computes a walking speed based on the body weight inputted by the body weight inputting means 49 and the assumed exercise stress level estimated by the assumed exercise stress level estimating means 43. More specifically, the walking speed computing means 44 comprises the CPU 9 out of the aforementioned units constituting the generator and computes the walking speed by substituting the assumed exercise stress level computed in the CPU 9 and the body weight inputted from the input unit 2 into the following expression (4):

$$Sw = b_1 \times (Wh \times Wt)^{1/2} + b_2 \quad (4)$$

wherein Sw represents a walking speed, Wh represents an assumed exercise stress level, Wt represents a body weight, and $b_1$ and $b_2$ represent coefficients (correction coefficients for changes based on several factors).

The body height inputting means 45 comprises the input unit 2 out of the aforementioned units constituting the generator and takes in a body height.

The walking pitch computing means 46 computes a walking pitch based on the body height inputted by the body height inputting means 45 and the walking speed computed by the walking speed computing means 44. More specifically, the walking pitch computing means 46 comprises the CPU 9 out of the aforementioned units constituting the generator and computes the walking pitch by substituting the walking speed computed in the CPU 9 and the body height inputted from the input unit 2 into the following expression (5):

$$Pw = c_1 \times (Sw \times H)^{1/2} + c_2 \quad (5)$$

wherein Pw represents a walking pitch, H represents a body height, and $c_1$ and $c_2$ represent coefficients (correction coefficients for changes based on several factors).

Figure 9:
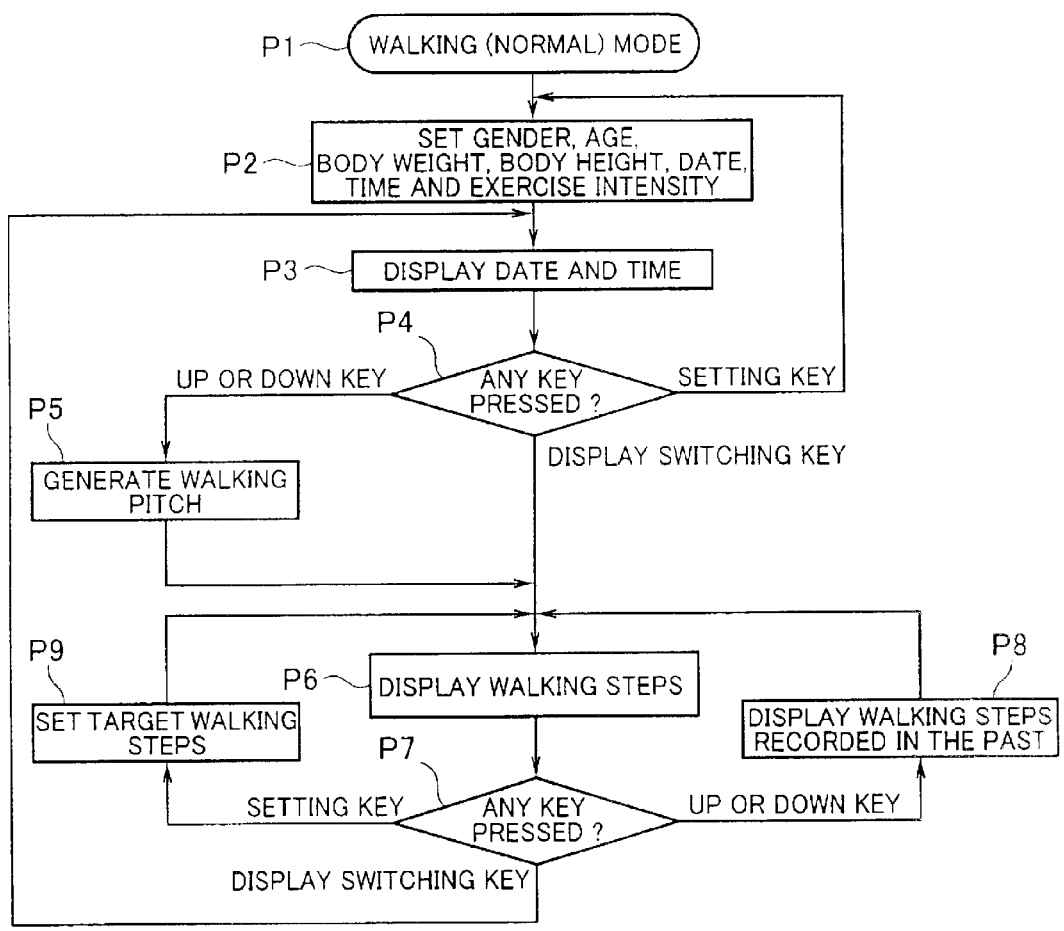
FIG. 9 is a flowchart illustrating procedural steps in a walking (normal) mode.

Next, the operations and actions of the walking pitch generator of the present invention will be described by use of FIG. 9 which is a flowchart showing procedural steps in a walking (normal) mode of the walking pitch generator according to the present invention and FIG. 6 which is a flowchart showing procedural steps in a physical strength estimating mode. In the above constitution of the present invention, the walking pitch generator is capable of not only generating a walking pitch at the time of walking but also counting walking steps and estimating physical strength (endurance). These features will also be described hereinafter.

Firstly, the procedural steps in the walking (normal) mode will be described in detail by use of FIG. 9.

Firstly, by setting a battery as a power source in the power unit 1, power is supplied to the units (STEP P1).

Subsequently, display images for initialization of gender, an age, a body weight, a body height, date, time and exercise intensity will be displayed. At this point, gender, an age, a body weight, a body height, date, time and exercise intensity are set in the order presented by switching and selecting numeric values or characters by means of the up key 2c or the down key 2d and setting the selected numeric value or characters by means of the setting key 2e (STEP P2).

Then, after completion of the initialization in STEP P2, the timekeeping unit 5 starts timing of time and the walking step detection unit 4 starts detection of walking step data. Then, in the CPU 9, the following various processes are performed based on the various data initialized in STEP P2, and the current date and time will be displayed on the display unit 8 (LCD 8a) (STEP P3).

As the various processes to be performed in the CPU 9, firstly, walking steps are computed based on the walking step data detected in the walking step detection unit 4. Then, if processes in steps in the physical strength estimating mode to be described later are not performed, a predetermined walking pitch stored in the storage unit 6 in advance is selected. Meanwhile, if the processes in the steps in the physical strength estimating mode to be described later are performed, a resting pulse rate (pulse rate corresponding to an exercise stress level of 0w) is estimated based on a relationship between pulse rates and exercise stress levels which is acquired in the body burden capacity acquiring means 41. Then, the estimated resting pulse rate and the exercise intensity and age inputted from the input unit 2 are substituted into the expression (2) so as to compute an assumed pulse rate. Then, the computed assumed pulse rate, two different pre-walking exercise stress levels (first exercise stress level and second exercise stress level) and two pre-walking pulse rates corresponding to these exercise stress levels (pre-walking pulse rate corresponding to the first exercise stress level and pre-walking pulse rate corresponding to the second exercise stress level) are substituted into the expression (3) so as to compute an assumed exercise stress level. Then, the computed assumed exercise stress level and the body weight inputted from the input unit 2 are substituted into the expression (4) so as to compute a walking speed. Then, the computed walking speed and the body height inputted from the input unit 2 are substituted into the expression (5) so as to compute a walking pitch.

Subsequently, if the setting key 2e is pressed with the date and time displayed on the display unit 8 (setting key in STEP P4), STEP P2 is repeated. Meanwhile, if the up key 2c or the down key 2d is pressed with the date and time displayed on the display unit 8 (up or down key in STEP P4), a sound is emitted from the buzzer 7b and light is emitted from the LED 7a at the walking pitch selected or computed in STEP P2 (STEP P5). A user can obtain a desired pulse rate by walking in synchronization with the sound and/or light emitted at the walking pitch. Meanwhile, if the display switching key 2b is pressed with the date and time displayed on the display unit 8 (display switching key in STEP P4), walking steps after the start of detection of the walking steps is displayed on the display unit 8 (STEP P6). The date and time are kept displayed on the display unit 8 until the setting key 2e, the up key 2c, the down key 2d or the display switching key 2b is pressed.

Then, if the up key 2c or the down key 2d is pressed with the walking steps displayed on the display unit 8 (up or down key in STEP P7), past walking steps are displayed (STEP P8). More specifically, each time the down key 2d is pressed down, walking steps of the previous day are displayed, and after dating back to one week ago, a total of the last one week is displayed, and then the current (today's) walking steps in STEP P6 are displayed again. As for the up key 2c, the series of display switchings for the down key 2d are reversed.

Further, if the setting key 2e is pressed with the walking steps displayed on the display unit 8 (setting key in STEP P7), the displayed screen image is switched to a screen image for setting target walking steps or a screen image for comparing with set target walking steps (STEP P9). More specifically, if target walking steps per day have not been set in the past, a screen image for setting the target walking steps will be displayed. After the target walking steps per day are set by switching from one numeric value to another and selecting a numeric value by means of the up key 2c or the down key 2d and setting the selected numeric value by means of the setting key 2e, STEP P6 where the current (today's) walking steps are displayed is carried out again.

Meanwhile, if the target walking steps per day have already been set in the past, an achievement ratio of the current (today's) walking steps to the target walking steps per day or a graph illustrating the achievement ratio is displayed as a screen image for comparing with the target walking steps per day. At the press of the setting key 2e, STEP P6 where the current (today's) walking steps are displayed is carried out again.

Meanwhile, if the display switching key 2b is pressed with the walking steps displayed on the display unit 8 (display switching key in STEP P7), STEP P3 where the current date and time are displayed is carried out again, and the subsequent steps are also carried out again. The walking steps are kept displayed on the display unit 8 until the up key 2c, the down key 2d, the setting key 2e or the display switching key 2b is pressed.

Next, the procedural steps in the physical strength estimating mode will be described in detail by use of FIG. 6.

At the press of the mode switching key 2a in any of the foregoing steps subsequent to STEP P3 in the walking (normal) mode, the walking (normal) mode is switched to the physical strength estimating mode (STEP T1).

Subsequently, a pulse rate is displayed on the display unit 8. Then, a user in a resting state (indicating an exercise stress level of 0) attaches the ear lobule attachable sensor 12 to his ear lobule. Thereby, pulse data at the time of resting (i.e., when an exercise stress level is 0) is detected in the pulse detection unit 3, and a pulse rate at the time of resting (i.e., when an exercise stress level is 0) is computed in the CPU 9 (STEP T2). This pulse rate at the time of resting (i.e., when an exercise stress level is 0) corresponds to the pre-walking pulse rate corresponding to the first exercise stress level (exercise stress level=0).

Then, a screen image for setting the height of a platform is displayed on the display unit 8. Then, the height of the platform is set by switching from one numeric value to another and selecting a numeric value by means of the up key 2c or the down key 2d and setting the selected numeric value by means of the setting key 2e (STEP T3).

Then, a constant ascending/descending pitch (e.g., 100 times/min) predetermined for ascending or descending the platform is outputted from the pitch output unit 7 (STEP T4).

Subsequently, the user ascends and descends the platform whose height has been set by the input unit 2 in synchronization with the constant ascending/descending pitch outputted from the pitch output unit 7. Thereby, pulse data while the user is ascending and descending the platform is detected in the pulse detection unit 3, and a pulse rate at the time of ascending and descending the platform is computed in the CPU 9 (STEP T5). This pulse rate at the time of ascending and descending the platform corresponds to the pre-walking pulse rate corresponding to the second exercise stress level.

Then, it is determined whether the pulse rate computed in the CPU 9 is stable within a given range (STEP T6). If the pulse rate is not stable (NO in STEP T6), STEP T5 is carried out again. Meanwhile, if the pulse rate is stable (YES in STEP T6), the body weight and the height of the platform which have been inputted from the input unit 2 and the constant ascending/descending pitch data stored in the storage unit 6 are substituted into the expression (1) so as to compute an exercise stress level at the time of ascending and descending the platform (STEP T7).

Then, the pulse rate at the time of resting (i.e., when an exercise stress level is 0) which has been computed in STEP T2, the pulse rate at the time of ascending and descending the platform which has been determined stable in STEP T6, and the exercise stress level at the time of ascending and descending the platform which has been computed in STEP T7 are substituted into the following expression (6) so as to compute PWC75% HRmax (STEP T8):

$$PWC = Ws \times (E-RHR)/HR-RHR \quad (6)$$

wherein PWC represents PWC75% HRmax, Ws represents an exercise stress level before walking (at the time of ascending and descending the platform), E represents 75% HRmax, HR represents a pulse rate at the time of ascending and descending the platform, and RHR represents a pulse rate at the time of resting (i.e., when an exercise stress level is 0).

Then, the CPU 9 refers to a physical strength evaluation table as exemplified in FIG. 7 which is categorized according to gender and ages and stored in the storage unit 6 in advance, specifies an evaluation comment corresponding to the gender and age inputted from the input unit 2 and the PWC75% HRmax which has been computed in the CPU 9 (STEP T9), and then returns to STEP T2 to measure a resting pulse rate. These steps are repeated until the mode switching key 2a is pressed again.

For one thing, as described above, the walking pitch generator of the present invention can estimate a pre-walking exercise stress level easily by inputting a body weight and the height of a platform from the body weight inputting means 49 and the height inputting means 50 and causing a user to ascend and descend the platform in synchronization with a constant ascending/descending pitch generated from the ascending/descending pitch generating means 51.

For another thing, the walking pitch generator of the present invention can securely obtain a relationship between biological data and exercise stress levels prior to walking from at least two points by obtaining a number of different pre-walking exercise stress levels and measuring biological data corresponding to each of these exercise stress levels by the biological data measuring means 48.

For another thing, the walking pitch generator of the present invention can securely obtain a pulse rate desired at the time of walking by adjusting exercise intensity in computation of an assumed pulse rate in the assumed biological data computing means 56 based on the exercise intensity inputted by the exercise intensity inputting means 53, an age inputted from the age inputting means 54 and a resting pulse rate acquired by the resting pulse rate acquiring means 55.

For another thing, the walking pitch generator of the present invention can obtain a walking pitch which provides a desired pulse rate at the time of walking by going through computation steps such as the assumed exercise stress level estimating means 43, the walking speed computing means 44 and the walking pitch computing means 46 based on the assumed pulse rate computed in the assumed biological data computing means 56 and the relationship between biological data and exercise stress levels which is acquired in the body burden capacity acquiring means 41.

In the above embodiment, the user is caused to ascend and descend the platform so as to obtain the relationship between biological data and exercise stress levels. The relationship can also be obtained by causing a user to keep walking at a constant pace or run a certain distance.

Further, although a pulse rate has been presented as an example of biological data, any other biological data which changes by walking activity such as a blood pressure may also be used.

As described above, according to the present invention, an assumed exercise stress level is estimated by relating an assumed pulse rate obtained by adjusting exercise intensity so as to be a desired pulse rate at the time of walking in the assumed biological data acquiring means to a relationship between biological data and exercise stress levels which is obtained before walking in the body burden capacity acquiring means, and a walking pitch which provides the desired pulse rate at the time of walking can be obtained by considering a body weight and a body height in addition to the assumed exercise stress level. As a result, a user can walk under an appropriate load.

Further, the relationship between biological data and exercise stress levels before walking can be obtained securely because biological data corresponding to a number of different exercise stress levels estimated by the pre-walking exercise stress level estimating means are measured by the biological data measuring means.

Further, in the pre-walking exercise stress level estimating means, a pre-walking exercise stress level can be estimated easily by inputting a body weight and the height of a platform from the body weight inputting means and the height inputting means, respectively, and causing a user to perform a simple task, i.e., ascend and descend the platform in synchronization with a constant ascending/descending pitch generated from the ascending/descending pitch generating means.

Further, by use of a pulse rate which is highly related to an exercise stress level and exhibits a significant change with respect to an exercise stress as biological data, particularly accurate and easy estimation can be made.

In addition, in the resting pulse rate acquiring means, a resting pulse rate can be obtained from the relationship between pulse rates and exercise stress levels which has already been acquired in the body burden capacity acquiring means, thereby make it possible to facilitate use thereof.

What is claimed is:

1. A system for estimating biological data at the time of walking, the system comprising:
    body burden capacity acquiring means,
    means for acquiring an exercise stress level at the time of walking, and
    means for estimating biological data at the time of walking,
    wherein:
    the body burden capacity acquiring means acquires a relationship between biological data and an exercise stress level prior to walking,
    the means for acquiring an exercise stress level at the time of walking acquires an exercise stress level at the time of walking, and
    the means for estimating biological data at the time of walking estimates biological data at the time of walking in correspondence to the exercise stress level acquired by the means for acquiring an exercise stress level at the time of walking based on the relationship acquired by the body burden capacity acquiring means.

2. The system of claim 1, wherein the body burden capacity acquiring means comprises:
    pre-walking exercise stress level estimating means, and
    biological data measuring means,
    wherein:
    the pre-walking exercise stress level estimating means estimates a number of different exercise stress levels prior to walking, and
    the biological data measuring means measures biological data corresponding to each of the different exercise stress levels estimated by the pre-walking exercise stress level estimating means.

3. The system of claim 2, wherein the pre-walking exercise stress level estimating means comprises:
    body weight inputting means,
    height inputting means,
    ascending/descending pitch generating means, and
    means for computing an exercise stress level at the time of ascending or descending a platform,
    wherein:
    the body weight inputting means takes in a body weight, the height inputting means takes in the height of the platform, the ascending/descending pitch generating means generates a constant ascending/descending pitch to ascend and descend the platform, and
    the means for computing an exercise stress level at the time of ascending or descending a platform computes an exercise stress level at the time of ascending or descending the platform based on the body weight inputted by the body weight inputting means, the height of the platform inputted by the height inputting means and the constant ascending/descending pitch generated by the ascending/descending pitch generating means.

4. The system of claim 1, wherein the means for acquiring an exercise stress level at the time of walking comprises:
    walking step measuring means,
    walking time measuring means,
    walking pitch computing means,
    body height inputting means,
    walking speed computing means,
    body weight inputting means, and
    means for computing an exercise stress level at the time of walking,
    wherein:
    the walking step measuring means measures walking steps at the time of walking,
    the walking time measuring means measures walking time during which the walking steps are measured by the walking step measuring means,
    the walking pitch computing means computes a walking pitch based on the walking steps measured by the walking step measuring means and the walking time measured by the walking time measuring means,
    the body height inputting means takes in a body height, the walking speed computing means computes a walking speed based on the walking pitch computed by the walking pitch computing means and the body height inputted by the body height inputting means,
    the body weight inputting means takes in a body weight, and the means for computing an exercise stress level at the time of walking computes an exercise stress level at the time of walking based on the walking speed computed by the walking speed computing means and the body weight inputted by the body weight inputting means.

5. The system of claim 2, wherein the means for acquiring an exercise stress level at the time of walking comprises:
    walking step measuring means,
    walking time measuring means,
    walking pitch computing means,
    body height inputting means,
    walking speed computing means, body weight inputting means, and means for computing an exercise stress level at the time of walking, wherein:

the walking step measuring means measures walking steps at the time of walking, the walking time measuring means measures walking time during which the walking steps are measured by the walking step measuring means, the walking pitch computing means computes a walking pitch based on the walking steps measured by the walking step measuring means and the walking time measured by the walking time measuring means, the body height inputting means takes in a body height, the walking speed computing means computes a walking speed based on the walking pitch computed by the walking pitch computing means and the body height inputted by the body height inputting means, the body weight inputting means takes in a body weight, and the means for computing an exercise stress level at the time of walking computes an exercise stress level at the time of walking based on the walking speed computed by the walking speed computing means and the body weight inputted by the body weight inputting means.

6. The system of claim 3, wherein the means for acquiring an exercise stress level at the time of walking comprises:

walking step measuring means, walking time measuring means, walking pitch computing means, body height inputting means, walking speed computing means, body weight inputting means, and means for computing an exercise stress level at the time of walking, wherein:

the walking step measuring means measures walking steps at the time of walking, the walking time measuring means measures walking time during which the walking steps are measured by the walking step measuring means, the walking pitch computing means computes a walking pitch based on the walking steps measured by the walking step measuring means and the walking time measured by the walking time measuring means, the body height inputting means takes in a body height, the walking speed computing means computes a walking speed based on the walking pitch computed by the walking pitch computing means and the body height inputted by the body height inputting means, the body weight inputting means takes in a body weight, and the means for computing an exercise stress level at the time of walking computes an exercise stress level at the time of walking based on the walking speed computed by the walking speed computing means and the body weight inputted by the body weight inputting means.

7. The system of claim 1, further comprising walking amount computing means for computing a walking amount by use of the biological data estimated by the means for estimating biological data at the time of walking.

8. The system of claim 2, further comprising walking amount computing means for computing a walking amount by use of the biological data estimated by the means for estimating biological data at the time of walking.

9. The system of claim 3, further comprising walking amount computing means for computing a walking amount by use of the biological data estimated by the means for estimating biological data at the time of walking.

10. The system of claim 4, further comprising walking amount computing means for computing a walking amount by use of the biological data estimated by the means for estimating biological data at the time of walking.

11. The system of claim 5, further comprising walking amount computing means for computing a walking amount by use of the biological data estimated by the means for estimating biological data at the time of walking.

12. The system of claim 6, further comprising walking amount computing means for computing a walking amount by use of the biological data estimated by the means for estimating biological data at the time of walking.

13. The system of claim 7, wherein the walking amount is at least one selected from exercise intensity, fat burning efficiency, a fat consumption calorie and an amount of burned fat.

14. The system of claim 8, wherein the walking amount is at least one selected from exercise intensity, fat burning efficiency, a fat consumption calorie and an amount of burned fat.

15. The system of claim 9, wherein the walking amount is at least one selected from exercise intensity, fat burning efficiency, a fat consumption calorie and an amount of burned fat.

16. The system of claim 10, wherein the walking amount is at least one selected from exercise intensity, fat burning efficiency, a fat consumption calorie and an amount of burned fat.

17. The system of claim 11, wherein the walking amount is at least one selected from exercise intensity, fat burning efficiency, a fat consumption calorie and an amount of burned fat.

18. The system of claim 12, wherein the walking amount is at least one selected from exercise intensity, fat burning efficiency, a fat consumption calorie and an amount of burned fat.

19. The system of any one of claims 1 to 18, wherein the biological data is a pulse rate.

20. A walking pitch generator comprising:

body burden capacity acquiring means, assumed biological data acquiring means, assumed exercise stress level estimating means, body weight inputting means, walking speed computing means, body height inputting means, and walking pitch computing means, wherein:

the body burden capacity acquiring means acquires a relationship between biological data and an exercise stress level prior to walking, the assumed biological data acquiring means acquires assumed biological data which represents biological data assumed to be desirably obtained at the time of walking, prior to walking, the assumed exercise stress level estimating means estimates an assumed exercise stress level representing an exercise stress level assumed to be obtained at the time of walking in correspondence to the assumed biological data acquired by the assumed biological data acquiring means based on the relationship acquired by the body burden capacity acquiring means, the body weight inputting means takes in a body weight, the walking speed computing means computes a walking speed based on the body weight inputted by the body weight inputting means and the assumed exercise stress level estimated by the assumed exercise stress level estimating means, the body height inputting means takes in a body height, and the walking pitch computing means computes a walking pitch based on the body height inputted by the body height inputting means and the walking speed computed by the walking speed computing means.

21. The walking pitch generator of claim 20, wherein the body burden capacity acquiring means comprises: pre-walking exercise stress level estimating means, and biological data measuring means, wherein:

the pre-walking exercise stress level estimating means estimates a number of different exercise stress levels prior to walking, and the biological data measuring means measures biological data corresponding to each of the different exercise stress levels estimated by the pre-walking exercise stress level estimating means.

22. The walking pitch generator of claim 21, wherein the pre-walking exercise stress level estimating means comprises:

the body weight inputting means, height inputting means, ascending/descending pitch generating means, and means for computing an exercise stress level at the time of ascending or descending a platform, wherein:

the height inputting means takes in the height of the platform, the ascending/descending pitch generating means generates a constant ascending/descending pitch to ascend and descend the platform, and the means for computing an exercise stress level at the time of ascending or descending a platform computes an exercise stress level at the time of ascending or descending the platform based on the body weight inputted by the body weight inputting means, the height of the platform inputted by the height inputting means and the constant ascending/descending pitch generated by the ascending/descending pitch generating means.

23. The walking pitch generator of any one of claims 20 to 22, wherein the biological data is a pulse rate.

24. The walking pitch generator of claim 23, wherein the assumed biological data acquiring means comprises:

exercise intensity inputting means, age inputting means, resting pulse rate acquiring means, and assumed biological data computing means, wherein:

the exercise intensity inputting means takes in exercise intensity desired at the time of walking, the age inputting means takes in an age, the resting pulse rate acquiring means acquires a resting pulse rate, and the assumed biological data computing means computes a pulse rate assumed to be desirably obtained at the time of walking based on the exercise intensity inputted by the exercise intensity inputting means, the age inputted by the age inputting means and the resting pulse rate acquired by the resting pulse rate acquiring means.

25. The walking pitch generator of claim 24, wherein the resting pulse rate acquiring means acquires, as the resting pulse rate, a pulse rate corresponding to an exercise stress level of zero based on the relationship acquired by the body burden capacity acquiring means.

* * * * *